United States Patent
de Silva et al.

(10) Patent No.: US 8,884,035 B2
(45) Date of Patent: Nov. 11, 2014

(54) PRODUCTION OF TETRAHYDROFURAN-2, 5-DIMETHANOL FROM ISOSORBIDE

(71) Applicant: E I du Pont de Nemours and Company, Wilmington, DE (US)

(72) Inventors: Wathudura Indika Namal de Silva, Wilmington, DE (US); Ekaterini Korovessi, Wilmington, DE (US); Carl Andrew Menning, Newark, DE (US); Joseph E Murphy, Woodbury, NJ (US); Joachim C Ritter, Wilmington, DE (US); Sourav Kumar Sengupta, Wilmington, DE (US); Christina S Stauffer, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/729,401

(22) Filed: Dec. 28, 2012

(65) Prior Publication Data

US 2013/0172586 A1    Jul. 4, 2013

Related U.S. Application Data

(60) Provisional application No. 61/582,076, filed on Dec. 30, 2011.

(51) Int. Cl.
   C07D 307/04 (2006.01)
   C07D 307/12 (2006.01)

(52) U.S. Cl.
   CPC ............ *C07D 307/12* (2013.01); *C07D 29/132* (2013.01)
   USPC ............................ 549/502; 549/429; 549/497

(58) Field of Classification Search
   CPC ..................................................... C07D 307/04
   USPC .......................................... 549/429, 497, 502
   See application file for complete search history.

(56) References Cited

U.S. PATENT DOCUMENTS

| | | |
|---|---|---|
| 2,082,025 A | 6/1937 | Peters, Jr. |
| 2,201,347 A | 5/1940 | Rittmeister |
| 2,440,929 A | 5/1948 | Frederick |
| 2,768,213 A | 10/1956 | Whetstone et al. |
| 3,070,633 A | 12/1962 | Utne et al. |
| 3,083,236 A | 3/1963 | Utne et al. |
| 3,189,651 A | 6/1965 | Ellery et al. |
| 3,215,742 A | 11/1965 | Horlenko et al. |
| 3,223,714 A | 12/1965 | Manly et al. |
| 3,268,588 A | 8/1966 | Horlenko et al. |
| 3,270,059 A | 8/1966 | Winderl et al. |
| 3,917,707 A | 11/1975 | Williams et al. |
| 3,933,930 A | 1/1976 | Dougherty, Jr. et al. |
| 4,254,059 A | 3/1981 | Grey |
| 4,400,468 A | 8/1983 | Faber |
| 4,401,823 A | 8/1983 | Arena |
| 4,780,552 A | 10/1988 | Wambach et al. |
| 5,112,994 A | 5/1992 | Koseki et al. |
| 5,210,335 A | 5/1993 | Schuster et al. |
| 5,412,111 A | 5/1995 | Matsumoto et al. |
| 5,538,891 A | 7/1996 | Schneider et al. |
| 5,696,303 A | 12/1997 | Darsow et al. |
| 5,981,769 A | 11/1999 | Baur et al. |
| 6,008,418 A | 12/1999 | Baur et al. |
| 6,087,296 A | 7/2000 | Harper et al. |
| 6,147,208 A | 11/2000 | Achhammer et al. |
| 6,265,602 B1 | 7/2001 | Voit et al. |
| 6,403,845 B1 | 6/2002 | Pfeffinger et al. |
| 6,407,294 B1 | 6/2002 | Breitscheidel et al. |
| 6,433,192 B1 | 8/2002 | Fischer et al. |
| 6,462,220 B1 | 10/2002 | Luyken et al. |
| 6,593,481 B1 | 7/2003 | Manzer |
| 6,818,781 B2 | 11/2004 | Bhatia |
| 7,019,155 B2 | 3/2006 | Manzer |
| 7,230,145 B2 | 6/2007 | Kadowaki et al. |
| 8,053,608 B2 | 11/2011 | Kouno et al. |
| 8,053,615 B2 | 11/2011 | Cortright et al. |
| 8,173,700 B2 * | 5/2012 | Frank et al. ................... 514/471 |
| 8,440,845 B2 * | 5/2013 | Makkee et al. ............... 549/464 |
| 8,501,989 B2 | 8/2013 | Boussie et al. |
| 8,524,925 B2 | 9/2013 | Sabesan et al. |
| 8,669,393 B2 | 3/2014 | Boussie et al. |
| 2003/0212298 A1 | 11/2003 | Brasse et al. |
| 2006/0014988 A1 | 1/2006 | Fischer et al. |
| 2007/0287845 A1 | 12/2007 | Lilga et al. |
| 2008/0200698 A1 | 8/2008 | Reichert et al. |
| 2009/0156841 A1 | 6/2009 | Sanborn et al. |

(Continued)

FOREIGN PATENT DOCUMENTS

CA    2800797 A1    12/2011
CN    101628875 A    1/2010

(Continued)

OTHER PUBLICATIONS

Corma, A. (1995) Chem. Rev., 95, 559-614.
Huber et al (2010) Journal of Catalysis, 270, 48-59.
Huber et al (2011) Journal of Catalysis, 279, 257-268.
Huber et al (2011) Green Chemistry, 13, 91
International Search Report dated Apr. 29, 2013, International Application PCT/US2012/071907
Blanc et al (2000), Green Chemistry, Apr. 2000, 89-91.
Trost, Barry M. 1992, American Chemical Society, 31.
Buntara, Teddy et al., Caprolactam from Renewable Resources: Catalytic Conversion of 5-Hydroxymethylfurfural into Caprolactone, Angewandte Chemie International Edition, 2011, pp. 1-6, vol. 50.

(Continued)

*Primary Examiner* — Golam M M Shameem

(57) ABSTRACT

Disclosed herein are processes comprising contacting isosorbide with hydrogen in the presence of a first hydrogenation catalyst to form a first product mixture comprising tetrahydrofuran-2,5-dimethanol. The processes can further comprise heating the first product mixture in the presence of hydrogen and a second hydrogenation catalyst to form a second product mixture comprising 1,6-hexanediol. The first and second hydrogenation catalysts can be the same or different.

15 Claims, No Drawings

(56) References Cited

U.S. PATENT DOCUMENTS

| | | |
|---|---|---|
| 2009/0314992 A1 | 12/2009 | Pinkos et al. |
| 2010/0113841 A1 | 5/2010 | Suzuki et al. |
| 2010/0216958 A1 | 8/2010 | Peters et al. |
| 2010/0274030 A1 | 10/2010 | Bevinakatti et al. |
| 2010/0317822 A1 | 12/2010 | Boussie et al. |
| 2011/0040131 A1 | 2/2011 | Kouno et al. |
| 2011/0071306 A1 | 3/2011 | Robinson |
| 2011/0218318 A1 | 9/2011 | Boussie et al. |
| 2011/0263916 A1 | 10/2011 | Bao et al. |
| 2011/0312051 A1 | 12/2011 | Kalnes et al. |
| 2012/0010419 A1 | 1/2012 | Pinkos et al. |
| 2012/0022298 A1 | 1/2012 | Pinkos et al. |
| 2012/0035399 A1 | 2/2012 | Abillard et al. |
| 2012/0059174 A1 | 3/2012 | Abillard et al. |
| 2012/0116122 A1 | 5/2012 | Feist et al. |
| 2012/0172579 A1 | 7/2012 | Qiao et al. |
| 2013/0172578 A1 | 7/2013 | Allgeier et al. |
| 2013/0172579 A1 | 7/2013 | Desilva et al. |
| 2013/0172580 A1 | 7/2013 | Ritter et al. |
| 2013/0172586 A1 | 7/2013 | Desilva et al. |
| 2013/0172629 A1 | 7/2013 | Allgeier et al. |
| 2013/0184495 A1 | 7/2013 | Dias et al. |
| 2013/0231505 A1 | 9/2013 | Allgeire et al. |
| 2013/0289311 A1 | 10/2013 | Allgeire et al. |
| 2013/0289312 A1 | 10/2013 | Allgeire et al. |
| 2013/0289318 A1 | 10/2013 | Allgeire et al. |
| 2013/0289319 A1 | 10/2013 | Allgeire et al. |
| 2014/0228596 A1 | 8/2014 | Allgeire et al. |

FOREIGN PATENT DOCUMENTS

| | | |
|---|---|---|
| CN | 102190639 A | 9/2011 |
| DE | 4238493 C1 | 4/1994 |
| EP | 0411403 A1 | 2/1991 |
| EP | 0418925 A2 | 3/1991 |
| EP | 110089 B1 | 1/1998 |
| EP | 1243573 A1 | 9/2002 |
| EP | 1243673 A1 | 9/2002 |
| EP | 2390247 A1 | 11/2011 |
| JP | 04041449 A | 2/1992 |
| JP | 04046133 A | 2/1992 |
| JP | 2003183200 A | 7/2003 |
| JP | 2006036653 A | 2/2006 |
| JP | 04555475 B2 | 9/2010 |
| KR | 100645668 B1 | 11/2006 |
| KR | 100688765 B1 | 2/2007 |
| WO | 9955654 A1 | 11/1999 |
| WO | WO2007103586 A2 | 9/2007 |
| WO | WO2007103586 A3 | 9/2007 |
| WO | WO2009126852 A1 | 10/2009 |
| WO | 2009133787 A1 | 11/2009 |
| WO | WO2010033789 A2 | 3/2010 |
| WO | 2010062689 A2 | 6/2010 |
| WO | 2010099201 A1 | 9/2010 |
| WO | 2010115759 A2 | 10/2010 |
| WO | 2010115759 A3 | 10/2010 |
| WO | 2010144873 A1 | 12/2010 |
| WO | 2011149339 A1 | 12/2011 |
| WO | 2013027766 A1 | 2/2013 |
| WO | 2013066776 A1 | 5/2013 |
| WO | 2013109477 A1 | 7/2013 |

OTHER PUBLICATIONS

Co-pending application published as 2013-0289311-A1.
Co-pending application published as US-2013-0172580-A1.
Co-pending application published as US-2013-0172629-A1.
Co-pending application published as US-2013-0289318-A1.
Co-pending application published as US-2013-0289312-A1.
Co-pending application published as US-2013-0289319-A1.
Co-pending application published as US-2013-0231505-A1.
Co-pending, U.S. Appl. No. 13/870,095.
Fogler Elements of Chemical Reaction Engineering, 2nd Edition, Prentice-Hail (1992) [Book].
International Search Report dated Mar. 29, 2013, PCT/US2012/062314.
International Search Report dated Apr. 29, 2013, PCT/US2012/071891.
International Search Report dated Apr. 29, 2013, PCT/US2012/071893.
International Search Report dated Apr. 29, 2013, PCT/US2012/071912.
International Search Report dated Apr. 30, 2013, PCT/US2012/071894.
International Search Report dated Jul. 26, 2013, PCT/US2013/038403.
International Search Report dated Jul. 18, 2013, PCT/US2013/038418.
International Search Report dated Jul. 24, 2013, PCT/US2013/038441.
International Search Report dated Jul. 24, 2013, PCT/US2013/038436.
office actions dated Jun. 26, 2013 and Sep. 13, 2013 for copending U.S Appl. No. 13/729,390.
office actions dated Sep. 27, 2013 and Dec. 17, 2013 for copending U.S. Appl. No. 13/729,464.
notice of allowance dated Oct. 1, 2013 for copending U.S. Appl. No. 13/729,494.
notice of allowance dated Nov. 19, 2013 for copending U.S. Appl. No. 13/729,401.
office action dated Dec. 20, 2013 for copending U.S. Appl. No. 13/729,507.
Co-pending U.S. Appl. No. 14/032,356, filed Sep. 19, 2013.
Co-pending U.S. Appl. No. 61/782,172, filed Mar. 14, 2013.
Co-pending U.S. Appl. No. 61/782,198, filed Mar. 14, 2013.
notice of allowance dated Jan. 13, 2014 for copending U.S. Appl. No. 13/729,494.
Database CAPLUS on STN, AN 1979:151575, Nishino et al, JP 53149905 A, Dec. 27, 1978 (abstract).
Database WPIX on STN, AN 1979-11181B [197906], Nishino et al, JP53149905 A Dec. 27, 1978 (abstract).
office action dated Apr. 9, 2014 for copending U.S. Appl. No. 13/870,080.
notice of allowance dated Apr. 25, 2014 for copending U.S. Appl. No. 13/729,464.
notice of allowance dated Apr. 28, 2014 for copending U.S. Appl. No. 13/729,494.
notice of allowance dated Apr. 29, 2014 for copending U.S. Appl. No. 13/729,507.
office action dated May 7, 2014 for copending U.S. Appl. No. 13/729,390.
copending application No. PCT/US14/23874 filed Mar. 12, 2014.
copending application No. PCT/US14/23905 filed Mar. 12, 2014.
Alamillo, R. et al., "Selective Hydrogenation of Biomass-Derived 5-Hydroxymethylfurfural Using Heterogeneous Catalysts", Green Chem., 2012, 14, 1413.
Jung, K.J. et al., "Furfural Decarbonylation Catalyzed by Charcoal Supported Palladium: Part I—Kinetics", Biomass 16 (1988) 63-76.
Jung, K.J. et al., "Furfural Decarbonylation Catalyzed by Charcoal Supported Palladium: Part II—A Continuous Process", Biomass 16 (1988) 89-96.
Lichtenthaler, F.W. "Carbohydrates as Organic Raw Materials" 2010 Wiley-VCH Verlag GmbH&Co. KGaA, Weinheim 10.1002/14356007.n05_n07.
Qin, L.-Z. et al., "Aqueous-phase deoxygenation of glycerol to 1,3-propanediol over $Pt/WO_3/ZrO_2$ catalysts in a fixed-bed reactor", Green Chem., 2010, 12, 1466-1472.
Rao, R.S. et al., "Furfural Hydrogenation Over Carbon-Supported Copper", Catalysis Letters 60 (1999) 51-57.
Zheng, H.-Y. et al., "Towards Understanding the Reaction Pathway in Vapour Phase Hydrogenation of Furfural to 2-Methylfuran", J Molecular Catalysis A: Chemical 246 (2006) 18-23.
Abe, R. et al. "Photocatalytic overall water splitting under visible light by TaON and $WO_3$ with an $IO_3^-/I^-$ shuttle redox mediator", Chem Commun, 2005, 3829-3831.
Adkins. H. et al, "The Catalytic hydrogenation of organic compounds over copper chromite", J Am Chem Soc (1931), vol. 53, 1093.

(56) References Cited

OTHER PUBLICATIONS

Alexeev, O S et al. "gamma-Al2O3-Supported Pt catalysts with extremely high dispersions resulting from Pt-W interactions", J Catal. 190 (2000) 157-17

Binder et al., "Simple chemical transformation of lignocellulosic biomass into furans for fuels and chemicals", J Am Chem Soc (2009) 131, 1979-1985.

Buntara, T. et al, "Caprolactam from Renewable Resources: Catalytic Conversion of 5-Hydroxymethylfuriural into Caprolactone", Angew. Chem. Int. Ed. (2011), 50(31), 7083-7087.

Buntara. T. et al., "From 5-hydroxymethylfurfural (HMF) to polymer precursors: catalyst screening studies on the conversion of 1,2,6-hexanetnol lo 1,6-hexanediol", Top Catal (2012) 55, 612-619.

Caes et al., "Conversion of Fructose into 5-(Hydroxymethyl)furfural in Sulfolane", ChemSusChem, (2011), 4(3), 353-356.

Chen, K. et al, "Chemoselective hydrogenolysis of tetrahydropyran-2-methanol to 1,6-hexanediol over rhenium-modified carbon-supported rhodium catalysis", ChemCatChem (2010) 2, 547-555.

Chen, K. et al, "C—O bond hydrogenolysis of cyclic ethers with OH groups over rhenium-modified supported iridium catalysts", J Catalysis (2012) vol. 294, 171-183.

Chia, M. et al, "Selective hydrogenolysis of polyols and cyclic ethers over bifunctional surface sites on rhodium-rhenium catalysts", J Am Chem Soc (2011) vol. 133, No. 32, 12675-12680.

Connor, R. et al, "Hydrogenolysis of Oxygenated Organic Compounds", J Am Chem Soc (1932), vol. 54, 4678-4690.

Diebold, U. "The surface science of titanium dioxide", Surface Science Reports 48 (2003) 53-229.

Efremov, A.A., "Transformations of leyoglucosenone at the anhydroglucoside bond", Chem Natural Compounds (1996) 34, 5, 582-589.

Co-pending application published as US-2013-0172629-A1.

Co-pending application published as US-2013-0289312-A1.

FOGLER Elements of Chemical Reaction Engineering, 2nd Edition, Prentice-Hall (1992) [Book].

International Search Report dated Apr. 29, 2013, PCT/US2013/071891.

notice of allowance dated Mar. 11, 2014 for copending U.S. Appl. No. 13/870,091.

notice of allowance dated Mar. 26, 2014 for copending U.S. Appl. No. 13/870,072.

Efremov, A.A. et al, "Conversions of Levoglucosenone in Acid Media", Sibirskii Khimicheskii Zhurnal, 1992, 6, 34-39 Translation.

Co-pending application published as US-2013-0172579-A1, filed Dec. 28, 2012.

Co-pending application published as US-2013-0172578-A1, filed Dec. 28, 2012.

Co-pending application published as US-2013-0172629-A1, filed Dec. 28, 2012.

Co-pending application published as US-2013-0172580-A1, filed Dec. 28, 2012.

Co-pending application published as US-2013-0289318-A1, filed Apr. 25, 2013.

Co-pending application published as US-2013-0289311-A1, filed Apr. 25, 2013.

Co-pending application published as US-2013-0289312-A1, filed Apr. 25, 2013.

Co-pending application published as US-2013-0289319-A1, filed Apr. 25, 2013.

Co-pending U.S. Appl. No. 13/870,095, filed Apr. 25, 2013.

Co-pending application published as US-2013-0231505-A1, filed Apr. 25, 2013.

office action dated Feb. 27, 2014 for copending U.S. Appl. No. 13/870,095.

office action dated Feb. 27, 2014 for copending U.S. Appl. No. 13/870,099.

Abe, R. et al, "Photocatalytic overall water splitting under visible light by TaON and WO3 with an IO3-/I- shuttle redox mediator", Chem Commun, 2005, 3829-3831.

Adkins, H. et al, "The catalytic hydrogenation of organic compounds over copper chromite", J Am Chem Soc (1931), vol. 53, 1093.

Alexeev, O.S. et al, "gamma-Al2O3-Supported Pt catalysts with extremely high dispersions resulting from Pt-W interactions", J Catal , 190 (2000) 157-17.

Buntara, T. et al, "Caprolactam from Renewable Resources: Catalytic Conversion of 5-Hydroxymethylfurfural into Caprolactone", Angew. Chem. Int. Ed. (2011), 50(31), 7083-7087.

Buntara, T. et al., "From 5-hydroxymethylfurfural (HMF) to polymer precursors: catalyst screening studies on the conversion of 1,2,6-hexanetriol to 1,6-hexanediol", Top Catal (2012) 55, 612-619.

Chen, K. et al, "Chemoselective hydrogenolysis of tetrahydropyran-2-methanol to 1,6-hexanediol over rhenium-modified carbon-supported rhodium catalysts", ChemCatChem (2010) 2, 547-555.

Chia, M. et al, "Selective hydrogenolysis of polyols and cyclic ethers over bifunctional surface sites on rhodium-rhenium catalysts", J Am Chem Soc (2011) vol. 133, No. 32, 12675-12680.

Efremov, A.A. et al, "Conversions of Levoglucosenone in Acid Media", Sibirskii Khimicheskii Zhurnal 92, 6, 34-39 Translation.

Efremov, A.A., "Transformations of levoglucosenone at the anhydroglucoside bond", Chem Natural Compounds (1998) 34, 5, 582-589.

Efremov, A.A. et al, "New thermocatalytic methods of chemicals producing from lignocellulosic materials in the presence of acid-type catalysts", Intl Symposium Wood Pulping Chemistry, 8th, Helsinki (1995) 689-696.

French, G.J. et al, "A re-investigation of the thermal decomposition of ammonium paratungstate", J. Mat. Sci, 16 (1981) 3427-3436.

Gong, L. et al, "Selective hydrogenolysis of glycerol to 1,3-propanediol over a Pt/WO3/TiO2/SiO2 catalyst in aqueous media", Appl Catal A General 390 (2010) 119-126.

Gong, X.Q. et al, "Small Au and Pt Clusters at the Anatase TiO2(101) Surface: Behavior at Terraces, Steps, and Surface Oxygen Vacancies", J. Am. Chem. Soc. 130 (2008) 370-381.

Helberger et al, Justus Liebigs Annalen der Chemie (1949) 561, 215-220.

Huang, L. et al, "Direct conversion of glycerol into 1,3-propanediol over Cu-H4SiW12O40/SiO2 in vapor phase", Catal Lett, 131 (2009) 312-320.

Jalil, P.A. et al, "A Study of Stability of Tungstophosphoric Acid, H3PW12O40, Using Synchrotron XPS, XANES, Hexane Cracking, XRD and IR Spectroscopy", J. Catalysis, 2003, 217(2), 292-297.

Jayaraman, S. et al, "Synthesis and Characterization of Pt-WO3 as Methanol Oxidation Catalysts for Fuel Cells", J Phys Chem B, 2005, 109, 22958-22966.

Jung, M.E. et al, "Synthesis of Methylene-Expanded 2',3'-Dideoxyribonucleosides", J Organic Chemistry 63 (1998) 8133-8144.

Kamalakar, G. et al, "tert-Butylation of Phenol over Ordered Solid Acid Catalysts in Supercritical Carbon Dioxide: Efficient Synthesis of 2,4-Di-tert-butylphenol and 2,4,6-Tri-tert-butylphenol", Ind Eng Chem Res, 45 (2006) 6118-6126.

Karinen, R. et al, "Biorefining: heterogeneously catalyzed reactions of carbohydrates for the production of furfural and hydroxymethyfurfural", Chem Sus Chem (2011) 4, 1002-1016.

Kaufmann, W.E. et al, "The use of platinum oxide as a catalyst in the reduction of organic compounds. IV. Reduction of furfural and its derivatives", J Am Chem Soc (1923) 45, 3029-3044.

Kiss, A.B. et al, "Thermal polycondensation of ammonium paratungstate, (NH4)10[W12O40(OH)2].4H2O", J. Materials Sci, 13 (1978) 2541-2547.

Koso, S. et al, "Chemoselective hydrogenolysis of tetrahydrofurfuryl alcohol to 1,5-pentanediol", Chem. Commun. (2009) 2035-2037.

Koso, S. et al, "Promoting effect of Mo on the hydrogenolysis of tetrahydrofurfuryl alcohol to 1,5-pentanediol over Rh/SiO2", J Catalysis 267 (2009), 89-92.

Kuba, S. et al, "Structure and properties of tungstated zirconia catalysts for alkane conversion", J Catalysis, 216 (2003) 353-361.

Lee, U. et al, "Structure of pentasodium trihydrogenhexatungstoplatinate(IV) icosahydrate", Acta Cryst. (1983) C39, 817-819.

(56) References Cited

OTHER PUBLICATIONS

Liu, L. et al, "Mesoporous WO3 supported Pt catalyst for hydrogenolysis of glycerol to 1,3-propanediol", Chin. J Catal., 2012, 33, 1257-1261.

Miftakhov, M.S. et al, "Levoglucosenone: the properties, reactions, and use in fine organic synthesis", Russian Chem Reviews (1994) 63(10) 869-882.

Nakagawa, Y. et al, "Heterogeneous catalysis of the glycerol hydrogenolysis", Catal Sci Technol 2011, 1, 179-190.

Nakagawa, Y. et al., "Production of 1,5-pentanediol from biomass via furfural and tetrahydrofurfuryl alcohol", Catalysis Today 195 (2012) 136-143.

Nikolla, E. et al., "'One-Pot' Synthesis of 5-(Hydroxymethyl)furfural from Carbohydrates Using Tin-Beta Zeolite", ACS Catal. (2011), 1, 408-410.

Okuhara, T. et al, "Insoluble heteropoly compounds as highly active catalysts for liquid-phase reactions", J. Mol. Catal. 74 (1992) 247-256.

Ott, L. et al, "Catalytic Dehydration of Glycerol in sub- and supercritical water: a new chemical process for acrolein production", Green Chemistry, 2006, pp. 214-220, vol. 8.

Pae, Y.I. et al, "Characterization of NiO-TiO2 modified with WO3 and catalytic activity for acid catalysis", Bull. Korean Chem. Soc. 2004, vol. 25(12), 1881-1888.

Ponder, G. R. et al, "Pyrolytic Conversion of Biomass of Anhydrosugars—Influences of Indigenous Ions and Polysaccharide Structures", Applied Biochem Biotech, 1990, vol. 24/25, p. 41-47.

Roman-Leshkov, Y. et al., "Solvent effects on fructose dehydration to 5-hydroxymethylfurfural in biphasic systems saturated with inorganic salts", Top Catal (2009) 52:297-303.

Shafizadeh, F. et al., "Some Reactions of Levoglucosenone", Carbohydrate Research, 1979, pp. 169-191, vol. 71.

SRI Process Economics Program, 31, Hexamethylenediamine Nov. 1967.

Ten Dam, J. et al, "Pt/Al2O3 catalyzed 1,3-propanediol formation from glycerol using tungsten additives", ChemCatChem (2013), 5(2), 497-505.

Tong, X. et al, "Biomass into chemicals: conversion of sugars to furan derivatives by catalytic processes", Appl. Catalysis A General, 385 (2010) 1-13.

Tripathy, P.K. et al, "A comparative study on the thermal decomposition of ammonium p-tungstate in batch and fluidized-bed reactors", Ind Eng Chem Res 36 (1997) 3602-3606.

Xu, W. et al, "Direct catalytic conversion of furfural to 1,5-pentanediol by hydrogenolysis of the furan ring under mild conditions over Pt/Co2AlO4 catalyst" Chem Comm, Royal Society of Chemistry (2011) vol. 47, No. 13, 3924-3926.

Yamazoe, S. et al, "XAFS Study of Tungsten L1-, L3- Edges: Structural Analysis of Loaded Tungsten Oxide Species", Envir Sci, Research Frontiers 2008, Spring 8, 138-139.

Yamazoe, S. et al, "XAFS Study of Tungsten L1- and L3-Edges: Structural Analysis of WO3 Species Loaded on TiO2 as a Catalyst for Photo-oxidation of NH3", J. Phys Chem C 2008, 112, 6869-6879.

Yoshinaga, Y. et al, "Shape-selective oxidation catalysed by a Pt-promoted ultramicroporous heteropoly compound", J.Chem. Soc. Faraday Trans 1998, 94(15) 2235-2240.

Zanardi, M.M. et al, "Synthesis of a simple chiral auxiliary derived from levoglucosenone and its application in a Diels-Alder reaction", Tetrahedron letters 50 (2009) 999-1002.

International Preliminary Report on Patentability, PCT International Application PCT/US2012/062314.

* cited by examiner

PRODUCTION OF TETRAHYDROFURAN-2, 5-DIMETHANOL FROM ISOSORBIDE

This application claims priority under 35 U.S.C. §119(e) from, and claims the benefit of, U.S. Provisional Application No. 61/582,076, filed Dec. 30, 2011, which is by this reference incorporated in its entirety as a part hereof for all purposes.

FIELD OF DISCLOSURE

Processes for preparing reaction mixtures comprising tetrahydrofuran-2,5-dimethanol from isosorbide are provided. Processes for preparing 1,6-hexanediol from reaction mixtures comprising tetrahydrofuran-2,5-dimethanol are also provided.

BACKGROUND

Industrial chemicals obtained from inexpensive sources are desirable for use in industrial processes, for example as raw materials, solvents, or starting materials. It has become increasingly desirable to obtain industrial chemicals or their precursors from materials that are not only inexpensive but also benign in the environment. Of particular interest are materials which can be obtained from renewable sources, that is, materials that are produced by a biological activity such as planting, farming, or harvesting. As used herein, the terms "renewable" and "biosourced" can be used interchangeably.

Tetrahydrofuran-2,5-dimethanol and related compounds are useful precursors in the synthesis of industrially useful chemicals such as pharmaceuticals, herbicides, stabilizers, and polymers. Tetrahydrofuran-2,5-dimethanol is useful in adhesives, sealants, coatings, solvents, resins, and polymer materials, for example. Tetrahydrofuran-2,5-dimethanol and compounds such as 1,2,6-hexanetriol and 2-hydroxymethyltetrahydropyran are also useful as intermediates in the synthesis of 1,6-hexanediol. 1,6-hexanediol is used in the production of polyesters for polyurethane elastomers, coatings, adhesives and polymeric plasticizers. 1,6-Hexanediol can also be converted to 1,6-hexamethylenediamine, a useful monomer in nylon production.

There is a need for processes to produce tetrahydrofuran-2,5-dimethanol from renewable biosources. There is a need for processes to produce tetrahydrofuran-2,5-dimethanol and 1,6-hexanediol from biomass-derived starting materials, including $C_6$ oxygenated hydrocarbons such as isosorbide.

SUMMARY

In one embodiment a process is provided, the process comprising: a) contacting isosorbide with hydrogen in the presence of a first hydrogenation catalyst at a first temperature between about 150° C. and about 400° C. and at a first pressure in the range of from about 500 psi to about 5000 psi to form a first product mixture comprising tetrahydrofuran-2,5-dimethanol.

In another embodiment, the process further comprises the step of: b) heating the first product mixture in the presence of hydrogen and a second hydrogenation catalyst at a second temperature between about 120° C. and about 350° C. to form a second product mixture comprising 1,6-hexanediol.

DETAILED DESCRIPTION

As used herein, where the indefinite article "a" or "an" is used with respect to a statement or description of the presence of a step in a process of this invention, it is to be understood, unless the statement or description explicitly provides to the contrary, that the use of such an indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), or both A and B are true (or present).

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; and through differences in the manufacture, source, or purity of the ingredients employed to make the compositions or carry out the methods. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, preferably within 5% of the reported numerical value.

As used herein, the term "biomass" refers to any hemicellulosic or lignocellulosic material and includes materials comprising hemicellulose, and optionally further comprising cellulose, lignin, starch, oligosaccharides and/or monosaccharides.

As used herein, the term "lignocellulosic" means comprising both lignin and cellulose. Lignocellulosic material may also comprise hemicellulose. In some embodiments, lignocellulosic material contains glucan and xylan.

Hemicellulose is a non-cellulosic polysaccharide found in lignocellulosic biomass. Hemicellulose is a branched heteropolymer consisting of different sugar monomers. It typically comprises from 500 to 3000 sugar monomeric units.

Lignin is a complex high molecular weight polymer and can comprise guaiacyl units as in softwood lignin, or a mixture of guaiacyl and syringyl units as in hardwood lignin.

As used herein, the term "sugar" includes monosaccharides, disaccharides, and oligosaccharides. Monosaccharides, or "simple sugars," are aldehyde or ketone derivatives of straight-chain polyhydroxy alcohols containing at least three carbon atoms. A pentose is a monosaccharide having five carbon atoms, and some examples are xylose, arabinose, lyxose and ribose. A hexose is a monosaccharide having six carbon atoms, and two examples are glucose and fructose. Disaccharide molecules (e.g., sucrose, lactose, fructose, and maltose) consist of two covalently linked monosaccharide units. As used herein, "oligosaccharide" molecules consist of about 3 to about 20 covalently linked monosaccharide units.

As used herein, the term "$C_n$ sugar" includes: monosaccharides having n carbon atoms; disaccharides comprising monosaccharide units having n carbon atoms; and oligosaccharides comprising monosaccharide units having n carbon atoms. Thus, "$C_6$ sugar" includes hexoses, disaccharides comprising hexose units, and oligosaccharides comprising hexose units.

As used herein, the term "$C_n$ sugar alcohol" refers to compounds produced from $C_n$ sugars by reduction of the carbonyl group to a primary or secondary hydroxyl group. Sugar alcohols having the general formula $H(HCHO)_{x+1}H$, are derived from sugars having the general formula $H(HCHO)_xHCO$. Monosaccharides and disaccharides can be used to form sugar alcohols, though the disaccharides are not fully hydrogenated. Three examples of sugar alcohols are xylitol ($C_5$), sorbitol ($C_6$), and mannitol ($C_6$).

As used herein, the abbreviation "ISOS" refers to isosorbide, also known as 1,4:3,6-dianhydrosorbitol and 1,4-dianhydrosorbitol. The chemical structure of isosorbide is represented by Formula (I).

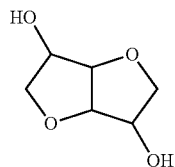

I

As used herein, the abbreviation "THFDM" or "TDM" refers to tetrahydro-2,5-furandimethanol, also known as 2,5-bis[hydroxymethyl]tetrahydrofuran and tetrahydrofuran-2,5-dimethanol, and includes a mixture of stereoisomers (cis- and racemic trans-isomers). The chemical structure of tetrahydro-2,5-furandimethanol is represented by Formula (II).

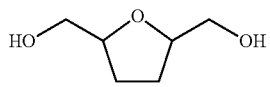

II

As used herein, the abbreviation "126HT" refers to 1,2,6-hexanetriol and includes a racemic mixture of isomers. The chemical structure of 1,2,6-hexanetriol is represented by Formula (III).

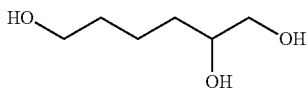

III

As used herein, the abbreviation "THPM" refers to tetrahydro-2H-pyran-2-methanol, also known as 2-hydroxymethyltetrahydropyran, and includes a racemic mixture of isomers. The chemical structure of tetrahydro-2H-pyran-2-methanol is represented by Formula (IV).

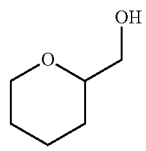

IV

As used herein, the abbreviation "1,6HD" refers to 1,6-hexanediol. The chemical structure of 1,6-hexanediol is represented by Formula (V).

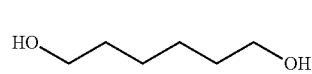

V

As used herein, the abbreviation "1,2CHD" refers to 1,2-cyclohexanediol and includes a mixture of stereoisomers (cis and racemic trans isomers). As used herein, the abbreviation "c12CHD" refers to cis-1,2-cyclohexanediol. As used herein, the abbreviation "t12CHD" refers to trans-1,2-cyclohexanediol. The chemical structure of 1,2-cyclohexanediol is represented by Formula (VI).

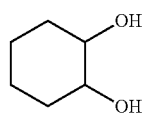

VI

As used herein, the abbreviation "1,5HD" refers to 1,5-hexanediol and includes a racemic mixture of isomers. The chemical structure of 1,5-hexanediol is represented by Formula (VII).

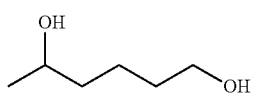

VII

As used herein, the abbreviation "1,5PD" refers to 1,5-pentanediol. The chemical structure of 1,5-pentanediol is represented by Formula (VIII).

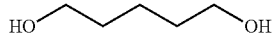

VIII

Disclosed herein are processes for obtaining tetrahydrofuran-2,5-dimethanol, 1,6-hexanediol, and mixtures of tetrahydrofuran-2,5-dimethanol and 1,6-hexanediol from isosorbide, which in turn can be derived from a renewable biosource. As used herein, the term "renewable biosource" includes biomass and animal or vegetable fats or oils.

Isosorbide can be obtained from $C_6$ sugar alcohols via an acid-catalyzed dehydration-cyclization reaction. See, for example published patent application WO 2007/103586 and WO 2009/126852. Suitable $C_6$ sugar alcohols include, for example, mannitol, sorbitol, galactitol, iditol, inositol, and mixtures comprising any of these. The $C_6$ sugar alcohols can be obtained from $C_6$ sugars which, in turn, can be derived from a renewable biosource containing lignocellulosic materials, for example corn grain, corn cobs, corn husks, corn stover, grasses, wheat, wheat straw, barley, barley straw, hay, rice straw, switchgrass, waste paper, sugar cane bagasse, sorghum, soy, trees, branches, roots, leaves, wood chips, sawdust, shrubs, bushes, vegetables, fruits, flowers, and mixtures of any two or more thereof. Products and by-products from the milling of grains are also suitable lignocellulosic materials for the production of $C_6$ sugars.

In the processes disclosed herein, isosorbide is contacted with hydrogen in the presence of a first hydrogenation catalyst at a first temperature and at a first pressure to form a first product mixture comprising tetrahydrofuran-2,5-dimethanol. In some embodiments, the first product mixture further comprises 1,6-hexanediol. In some embodiments, the first product mixture further comprises one or more of 1,2,6-hexanetriol and 2-hydroxymethyltetrahydropyran. In some embodiments, the processes further comprise heating the first product mixture in the presence of hydrogen and a second hydrogenation catalyst at a second temperature to form a second product mixture comprising 1,6-hexanediol. In some embodiments, the second product mixture further comprises one or more of 1,2,6-hexanetriol, 1,2-cyclohexanediol, 1,5-pentanediol, and 1,5-hexanediol.

The isosorbide, hydrogen, and first hydrogenation catalyst are contacted at a first temperature between about 150° C. and about 400° C. and at a first pressure between about 500 psi and about 5000 psi for a time sufficient to form a first product mixture comprising THFDM. In some embodiments, the first temperature is between about 200° C. and about 290° C. In some embodiments, the first temperature is between and optionally includes any two of the following values: 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 340° C., 350° C., 360° C., 370° C., 380° C., 390° C., and 400° C.

Hydrogen, optionally in combination with an inert gas such as nitrogen or argon, is contacted with the isosorbide and the first hydrogenation catalyst at a total applied pressure, referred to herein as "the first pressure", between about 500 psi and 5000 psi. In an embodiment, the first pressure is between about 1000 psi and about 2000 psi. In some embodiments, the first pressure is between and optionally includes any two of the following values: 500, 600, 700, 800, 900, 1000, 1100, 1200, 1300, 1400, 1500, 1600, 1700, 1800, 1900, 2000, 2500, 3000, 3500, 4000, 4500, and 5000 psi. If an inert gas is used in combination with the hydrogen, the amount of the inert gas should be such that it does not negatively impact the formation of the first product mixture.

For contacting with hydrogen in the presence of a first hydrogenation catalyst, the isosorbide is typically dissolved or suspended in a liquid medium, referred to herein as a "solvent". Suitable solvents include water, a $C_1$-$C_{20}$ alcohol, a $C_2$-$C_{20}$ ether, a $C_2$-$C_{20}$ ester, or mixtures thereof. Examples of suitable alcohols which are commercially available include methanol, ethanol, propanol, butanol, and hexanol. Examples of suitable ethers which are commercially available include dibutylether, dihexylether, methyl-t-butyl-ether, tetrahydrofuran, and dioxane. Examples of suitable esters which are commercially available include ethyl acetate, butyl acetate, methyl butyrate, ethyl butyrate, butyl butyrate and hexyl acetate.

The concentration of isosorbide in the solvent, whether dissolved or as a suspension, is between about 1 wt % and about 50 wt %; in some embodiments it is between and optionally includes any two of the following values: 1 wt %, 5 wt %, 10 wt %, 15 wt %, 20 wt %, 25 wt %, 30 wt %, 35 wt %, 40 wt %, 45 wt %, and 50 wt %. It is anticipated that higher concentrations of isosorbide in water, or even neat isosorbide, could be used. The optimal concentration will depend on the intended reaction conditions.

At the end of the designated contacting time, if desired, the first hydrogenation catalyst can be separated from the first product mixture by methods known in the art, for example by filtration. After separation from the catalyst, if desired the first product mixture components can be separated from one another using any appropriate method known in the art, for example distillation. In addition to tetrahydrofuran-2,5-dimethanol and 1,6-hexanediol, the first reaction mixture components can also include 2-hydroxymethyltetrahydropyran and/or 1,2,6-hexanetriol.

The first product mixture is then heated in the presence of hydrogen and a second hydrogenation catalyst at a second temperature to form a second product mixture comprising 1,6-hexanediol. In one embodiment, the first product mixture is dissolved or suspended in a solvent, which can be the same or different from any solvent used with the isosorbide in the first step of the process. In one embodiment, the first product mixture is used without any added solvent.

The second temperature is between about 120° C. and about 350° C., for example between about 200° C. and about 290° C. In some embodiments, the temperature is between and optionally includes any two of the following values: 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., and 350° C.

Hydrogen, optionally in combination with an inert gas such as nitrogen or argon, is present during the heating of the first product mixture in the presence of the second hydrogenation catalyst. The total applied pressure can range from 500 psi to about 5000 psi. In an embodiment, the pressure is between about 1000 psi and about 2000 psi. In some embodiments, the applied pressure is between and optionally includes any two of the following values: 500, 600, 700, 800, 900, 1000, 1100, 1200, 1300, 1400, 1500, 1600, 1700, 1800, 1900, 2000, 2500, 3000, 3500, 4000, 4500, and 5000 psi. If an inert gas is used in combination with the hydrogen, the amount of the inert gas should be such that it does not negatively impact the formation of the second product mixture.

At the end of the designated heating time, if desired, the second hydrogenation catalyst can be separated from the second product mixture by methods known in the art, for example by filtration. After separation from the catalyst, if desired the product mixture components, including one or more of 1,6-hexanediol, 1,2,6-hexanetriol, 2-hydroxymethyl-5-hydroxytetrahydropyran, 1,2-cyclohexanediol, 1,5-pentanediol, and 1,5-hexanediol can be separated from one another using any appropriate method known in the art, for example distillation. In one embodiment, the second product mixture comprises 1,6-hexanediol. In one embodiment, the second product mixture comprises 1,2,6-hexanetriol. In one embodiment, the second product mixture comprises 2-hydroxymethyl-5-hydroxytetrahydropyran. In one embodiment, the second product mixture comprises 1,2-cyclohexanediol. In one embodiment, the second product mixture comprises 1,5-pentanediol. In one embodiment, the second product mixture comprises 1,5-hexanediol.

In one embodiment, the first and second hydrogenation catalysts are different. In one embodiment, the first and second hydrogenation catalysts are the same. In one embodiment, the second hydrogenation catalyst comprises the first hydrogenation catalyst.

Hydrogenation catalysts suitable for use in the processes disclosed herein include conventional hydrogenation catalysts selected from platinum, palladium, copper, nickel, cobalt, silver, ruthenium, rhodium, iron and mixtures thereof. Optionally, the hydrogenation catalysts further comprise a solid support, for example carbon; an oxide such as $WO_3$, $SiO_2$, $Al_2O_3$, $TiO_2$, $ZrO_2$, and mixtures thereof; montmorillonite or other clay; or an H—Y or other zeolite.

In some embodiments, the first and/or second hydrogenation catalyst comprises CuO. In some embodiments, the catalyst comprises from 2 wt % to 98 wt % CuO and further comprises from 98 wt % to 2 wt % of at least one oxide selected from the group consisting of zinc oxide (ZnO), magnesium oxide (MgO), barium oxide (BaO), chromium oxide ($Cr_2O_3$), silica ($SiO_2$), alumina ($Al_2O_3$), zirconium dioxide ($ZrO_2$), nickel oxide (NiO), manganese oxide ($MnO_2$), sodium oxide ($Na_2O$), potassium oxide ($K_2O$), cerium oxide ($CeO_2$), lanthanum oxide ($La_2O_3$), iron oxide ($Fe_2O_3$), silver oxide ($Ag_2O$) and cobalt oxide ($Co_2O_3$), based on the total weight of the catalyst. In one embodiment, the catalyst further comprises ZnO. In one embodiment, the catalyst further comprises MgO. In some embodiments, the catalyst further comprises carbon. Examples of suitable commercially available catalysts include but are not limited to the following: CuO/ZnO, $BaO/CuO/Cr_2O_3/SiO_2$, $BaO/CuO/Cr_2O_3$, $BaO/CuO/MnO_2/Cr_2O_3$, $CuO/SiO_2$, $CuO/Al_2O_3$, $CuO/NiO/Al_2O_3$, $CuO/Cr_2O_3/MnO_2$, $CuO/Cr_2O_3$, $CuO/MnO_2$, $CuO/Cr_2O_3$, $CuO/ZnO/Al_2O_3$, $CuO/SiO_2/Cr_2O_3/MgO$, $CuO/ZnO/CeO_2/Al_2O_3/Na_2O/C$, CuO/NiO, and $NiO/CuO/K_2O/Cr_2O_3/CaF_2$. In one embodiment, the catalyst comprises CuO/ZnO, $CuO/ZnO/Al_2O_3$, or $CuO/ZnO/CeO_2/Al_2O_3/Na_2O/C$. In one embodiment, the catalyst comprises $CuO/ZnO/Al_2O_3$.

Catalysts comprising CuO and at least one oxide as described above can be prepared by forming a co-precipitated catalyst comprising compounds which are thermally decomposable to oxides or mixed oxides.

The precipitated catalyst can be formed by admixing solutions of the elements and heating the resultant mixture to its precipitation temperature; separately heating a solution of a precipitant in water; and thereafter adding both solutions to preheated demineralized water with vigorous stirring and strict pH control, for example in a precipitation reactor. Alternatively, the precipitate can be formed by admixing solutions of the elements and heating the resultant mixture to its precipitation temperature; then adding the preheated mixture or solution of elements rapidly to a predetermined volume of a preheated solution of a precipitant in water. In yet another method of forming a precipitated catalyst, the precipitate can be formed by admixing solutions of the elements and heating the resultant mixture to its precipitation temperature; then adding a preheated solution of precipitant in water (preheated to a predetermined precipitation temperature) to the hot solution or mixture of the elements with vigorous stirring, until the desired pH value of combined solutions is reached. In all methods, the precipitant can be a solution of sodium, potassium and/or ammonium carbonate or bicarbonate in water.

The precipitation can be carried out at high temperature, for example between about 75° C. and 100° C. Lower temperatures, for example between about 50° C. and 60° C., can also be used, but the crystallite size of the catalyst precursor so formed is larger, and the activity of such a catalyst may be lower. The precipitation can be effected at a pH in the range of 6.5-9.5.

After maintaining the stirred solution at the precipitation temperature for a period of time between about 0.5 and 60 minutes, the precipitate can then be separated from the residual liquid. The separation can be effected by filtration. The precipitate can be re-suspended at least once, but typically a few times, in demineralized water, then separated from the water by filtration, and finally washed thoroughly on the filter.

The washed precipitate comprising a homogeneous hydrated catalyst precursor can then be dried by any known drying process, for example in an oven at temperatures between 50° C. and 130° C., under vacuum or at normal pressure. Alternatively, spray drying can be employed.

The dried precipitate, also referred to herein as a precursor, comprises an essentially homogeneous association of carbonates and hydroxycarbonates with a potential oxide content of between 65% and 80%. As described above herein, the elements may initially be in soluble nitrate form or optionally in the form of a thermally decomposable ammonium salt. The dried precipitate can be calcined to provide a catalyst.

The calcination can comprise treating the dried precipitate at a temperature of between 200° C. and 450° C., for example between 250° C. and 350° C., for between 3 and 10 hours, to obtain a homogeneous catalyst.

The homogeneous catalyst can be densified and pelletized after addition of 1-3 wt %, for example about 2 wt %, graphite. It can also be made into extrudates using, for example, methyl cellulose as a binder. The homogeneous catalyst can also be sieved to a desired particle size distribution to be used in batch or continuous stirred tank reactors.

The copper component of the active catalyst contains the copper in a dispersed form, and after activation acts primarily as the active constituent of the catalyst, while the additional oxide component(s) acts primarily, but not exclusively, as a structural support. An oxide of chromium, zinc, manganese, or barium when present, thus enhances the activity and/or selectivity of the catalyst and its resistance to poisons, while aluminum oxide, zirconium oxide, and silica enhances the stability, abrasion or attrition resistance, mechanical strength, and thermal stability of the active catalyst.

The active catalyst can be reduced by thermal activation to produce an active catalyst in which at least a portion of the copper and other element(s) present in the catalyst are in metallic form.

The thermal activation can comprise reduction treatment of the calcined catalyst in a reactor, using a mixture of an inert gas, preferably nitrogen, and at least one reducing gas, such as hydrogen, carbon monoxide or a mixture thereof. The molar ratio between reducing gas and inert gas should be between 1:30 and 1:100. The reduction temperature can be between 100° C. to 280° C., preferably between 130° C. and 240° C., and the pressure can be 0.1 to 1 MPa.

The catalyst is preferably first slowly heated at a rate of between 30-50° C./hour under the inert gas at a pressure between 0.6-0.9 MPa, until a temperature between 120° C. and 150° C. has been reached. Thereafter the reduction takes place by adding the reducing gas to the inert gas in a molar ratio as described above, but preferably between 1:50 and 1:40. The temperature is then slowly further increased at a rate of 15-25° C./hour to reach a temperature between 190 C.° and 210° C. The thermal reductive activation is continued at this temperature for a time period of between 10 and 24 hours. Thereafter, in a final step, the temperature can be increased to between 230° C. and 250° C. and the molar ratio of reducing gas to inert gas adjusted to between 1:10 and 1:6 for a time period of 1-3 hours, in order to complete activation. The reduced catalyst can then be stabilized by passivating the catalyst in a mixture of nitrogen and oxygen to prevent complete oxidation of the catalyst when exposed to air.

In another embodiment, a wide range of commercially available catalyst supports comprising metal oxides, mixed metal oxides or metal-incorporated metal oxides (such as gamma-alumina, La-doped alumina, Ce-doped zirconia, magnesium oxide, and USY zeolite) can be used as supports with the CuO catalyst.

The metals so incorporated in the metal oxide or mixed metal oxide support can be an alkali, an alkaline earth metal, a rare earth metal, or a mixture of one or more such metals. Incorporation of the specified metal or metals onto the metal oxide or mixed metal oxide support can be accomplished by impregnating the support with an aqueous solution of water-soluble salt precursor(s) of metal(s) such as nitrates and acetates by known methods, drying the wetted support, and then calcining the combination of the metal salt(s) and metal oxide or mixed metal oxide support at a temperature of 350° C. up to 600° C. for about 2 to 16 hours to produce a metal-modified metal oxide or mixed metal oxide support(s). The calcining step at 250° C. to 600° C. prior to depositing the copper on the support is necessary. The time of calcining should be sufficient to decompose the metal salt(s) to the metal oxide(s). The total amount of added metal(s) in the support is in the range of 0.5% to 20% by weight, based upon the weight of the support.

After incorporation of the metal(s), copper, preferably as copper nitrate, is impregnated on the metal-modified metal oxide or mixed metal oxide support. The amount of copper deposited will depend on the desired activity of the catalyst, and can be as little as 2% by weight to as much as 20% by weight. The final catalyst composition containing the copper catalyst on the modified support can be in the form of powder, granules, extrudates or tablets, but certain specific characteristics such as surface area and pore volume, for example, are modified by reason of the deposit of copper.

In another embodiment, the catalyst comprising active metal(s) in the co-precipitated form with other elements, or active metal(s) dispersed on a first oxide, mixed metal oxides or metal-modified metal oxide support, as described herein above, can be either physically mixed and sieved to appropriate size, or intimately mixed and optionally co-extruded or pelletized with a second metal oxide, mixed metal oxides or metal-modified metal oxide support. The pelletized or co-extruded catalyst can be optionally crushed and sieved to appropriate size for use in slurry batch, continuous stirred tank, or fixed bed reactors.

The first and second steps of the processes can be run in batch or continuous modes, in liquid phase, gas phase, or biphasic conditions. In a batch or continuous mode of operation, the amount of each catalyst used will depend on the specific equipment configuration and reaction conditions. The processes can be carried out in standard reactors as are known in the art. In one embodiment, the processes are run in at least one trickle bed reactor.

In an embodiment of continuous operation, the reaction(s) can be carried out in a trickle bed reactor, wherein the liquid hourly space velocity is between 0.05 and 10 $h^{-1}$ (mL liquid feed/mL catalyst/h). In another embodiment, the range for liquid hourly space velocity is from 0.5 to about 5 $h^{-1}$ (mL liquid feed/mL catalyst/h). In an embodiment of continuous operation, the reaction(s) can be carried out in a trickle bed reactor, wherein the ratio of the gas volumetric flowrate to the liquid volumetric flowrate as measured at ambient conditions (gas to oil ratio) is between 100 and 5,000, for example from 1,000 to about 4,000.

EXAMPLES

The methods described herein are illustrated in the following Examples. From the above discussion and these Examples, one skilled in the art can ascertain the essential characteristics of this invention, and without departing from the spirit and scope thereof, can make various changes and modifications of the invention to adapt it to various uses and conditions.

The following abbreviations are used in the examples: "° C." means degrees Celsius; "wt %" means weight percent; "g" means gram(s); "min" means minute(s); "h" means hour(s); "µL" means microliter(s); "wt %" means weight percent; "RV(s)" means reaction vessel(s); "psi" means pounds per square inch; "mg/g" means milligram(s) per gram; "µm" means micrometer(s); "mL" means milliliter(s); "mm" means millimeter(s); "cm" means centimeter(s); "mL/min" means milliliter(s) per minute; "MPa" means megapascal(s); "GC" means gas chromatography; "MS" means "mass spectrometry"; "Conv" means conversion; "LHSV" means liquid hourly space velocity, "1,2PDO" means 1,2-propanediol and "GTO" means gas to oil ratio.

Materials

All commercial materials were used as received unless stated otherwise. Isosorbide (purity 98%) in examples 1-8 was purchased from Aldrich (St. Louis, Mo.). Isosorbide (assay >98%) for all other examples was obtained from ABCR GmbH & Co, KG, Karlsruhe, Germany. Tetrahydrofuran-2,5-dimethanol (>95%) for all examples was obtained from (Penn A Kem, Memphis, Tenn.). Deionized water was used unless otherwise indicated. Commercial catalysts, catalyst supports and other materials used for catalyst preparation, or in the Examples, are described in the list below. In some Examples, the materials are referred to by the letter designation shown in the "Material Identifier" column.

Table of Commercially Available Materials Used and Their Sources

| Material Identifier | Description | Vendor | Catalog Number | Composition (wt %) |
|---|---|---|---|---|
| A | BaO/CuO/$Cr_2O_3$/$SiO_2$ | SuedChemie | G-22/2 | CuO 47%, $Cr_2O_3$ 34%, BaO 6%, $SiO_2$ 13% |
| B | BaO/CuO/$Cr_2O_3$ | SuedChemie | G-22 | CuO 41%, $Cr_2O_3$ 43%, BaO 12% |
| C | BaO/CuO/$MnO_2$/$Cr_2O_3$ | SuedChemie | G-99B-0 | CuO 47%, $Cr_2O_3$ 46%, $MnO_2$ 4%, BaO 2% |
| D | CuO/$Cr_2O_3$ | SuedChemie | T-4466 | CuO 53%, $Cr_2O_3$ 45% |
| E | CuO/$MnO_2$ | SuedChemie | T-4489 | CuO 56%, $MnO_2$ 10%, $Al_2O_3$ 34% |
| F | CuO/ZnO/$Al_2O_3$ | SuedChemie | ActiSorb ® 301 | CuO 53%, ZnO 27%, $Al_2O_3$ 20% |
| G | CuO/ZnO | SuedChemie | T-2130 | CuO 33%, ZnO 66% |

Table of Commercially Available Materials Used and Their Sources

| Material Identifier | Description | Vendor | Catalog Number | Composition (wt %) |
|---|---|---|---|---|
| H | $CuO/Cr_2O_3/MnO_2$ | BASF | Cu-1950P | Copper Chromite 73%, Copper Oxide 21%, Manganese Oxide 5%, Chromium (6+) <0.3% |
| I | $CuO/SiO_2$ (BASF Cu-0860) | BASF | Cu-0860 | Decan-1-ol 30.0-50.0%, Copper 25.0-40.0%, Silicon dioxide 10.0-20.0%, Calcium oxide 0.0-10.0%, Copper oxide 0.0-10.0%, Palygorskite 7 0.0-7.0%, Crystalline silica 0.0-1.0% |
| J | $CuO/SiO_2$ (Evonik CPCAT 9/1593) | Evonik | CPCAT 9/1593 | CuO 0-40%, $Cu_2O$ 0-40%, $Na_2O_3Si$ 0-5%, $SiO_2$ >40% |
| K | $CuO/NiO/Al_2O_3$ | Evonik | CPCAT 9/1596 | $Al_2O_3$ 45-90%, $Cr_2O_3$ 0-5%, CuO 0-25%, NiO 0-25% |
| L | $CuO/Al_2O_3$ | Evonik | CPCAT 9/1597 | $Al_2O_3$ 45-90%, $Cr_2O_3$ 0-5%, CuO 0-25% |
| M | $CuO/ZnO/CeO_2/Al_2O_3/Na_2O/C$ | Johnson Matthey | PRICAT CZ 30/18 T 6 * 5 mm | |
| N | $CuO/SiO_2/Cr_2O_3/MgO$ | Johnson Matthey | PRICAT CU 60/35 P | CuO 78%, $SiO_2$ 14.5%, $Cr_2O_3$ 1.5%, MgO 3%, $H_2O$, $CO_2$ Balance |
| O | CuO/NiO | Shepherd Chemical | LB 3307 | Cu 27.5%, Ni 26.5%, Balance Carbonate |
| P | HY CBV780 | Zeolyst | CBV780 | $SiO_2/Al_2O_3$ mole ratio = 80:1 |
| Q | $ZrO_2$ | Saint-Gobain NorPro | SZ31107 | |
| R | $Nb_2O_5$ | Aldrich | # 208515 | |
| S | Sasol Alumina 3% La | Sasol | PURALOX SCFa-140/L3 | Sasol Alumina doped with 3% Lanthanum |
| T | Sasol Alumina 10% La | Sasol | PURALOX SCFa-140/L10 | Sasol Alumina doped with 10% Lanthanum |
| U | MEL Ce/$ZrO_2$ | MEL Chemicals | XZO 1291-Ce/$ZrO_2$ | $CeO_2$ 15%, $La_2O_3$ 4.4% |
| V | MgO | Sigma-Aldrich Chemie GmbH | 34.279-3 | |
| W | Mg30HTC | Sasol | Pural MG30 | |
| X | $ZrO_2WO_3$ | MEL Chemicals | XZO 1250 | 15% $WO_3$ (on $ZrO_2$ basis) |
| | $La(NO_3)_3 \times XH_2O$ | Sigma-Aldrich Chemie GmbH | 018545-238554 | X = 3-5 |
| | $Ba(NO_3)_2$ | Sigma-Aldrich Chemie GmbH | 217581 | 99.1% purity |
| | $Cu(NO_3)_2 \times 2.5H_2O$ | Sigma-Aldrich Chemie GmbH | 12837 | 98.2% purity |

The commercial catalysts obtained as shaped materials (tablets, extrudates, spheres etc.) were crushed and sieved to 0.125-0.160 mm prior to loading into the continuous reactor. The commercial catalysts obtained in powder form were press pelleted, crushed and sieved to 0.125-0.160 mm prior to loading in the continuous reactor.

Catalyst Preparation Method I

Catalyst samples referred to as "Catalyst A intimately mixed with Catalyst B" were prepared using the following procedure: If either catalyst A or catalyst B was originally a shaped material (tablets, extrudates, spheres, etc.), it was first crushed to powder form (<125 μm). Four mL of each catalyst were combined and mixed together in a 25 mL glass vial by shaking for a minimum of 30 seconds. The mixture was then screened using a 250 μm sieve. The sieved material was press-pelleted, crushed and sieved to 0.125-0.160 mm prior to loading into the continuous reactor.

Catalyst Preparation Method II

Catalyst samples referred to as "Catalyst A separately mixed with Catalyst B" were prepared using the following procedure: If either catalyst A or catalyst B was originally a shaped material (tablets, extrudates, spheres, etc.), it was first crushed and sieved to 0.125-0.160 mm. If either catalyst A or catalyst B was originally in powder form it was first press-pelleted, crushed and sieved to 0.125-0.160 mm. Four mL of each catalyst were combined and mixed together in a 25 mL glass vial by shaking for minimum of 30 seconds.

Catalyst Preparation Method III

Catalyst samples referred to as "supported copper catalysts" were prepared using the following procedure: Supports used in this catalyst preparation method include: Sasol Alumina 3% La, Sasol Alumina 10% La, MEL Ce/$ZrO_2MgO$, and HY CBV780. If the support was originally a shaped material (tablets, extrudates, spheres, etc.), it was crushed and sieved to 0.125-0.160 mm. If the support was originally in powder form it was press-pelleted, crushed and sieved to 0.125-0.160 mm. The support was optionally impregnated with La or Ba at ambient conditions, in a porcelain dish mixed in a lab-shaker with the appropriate concentration of $La(NO_3)_3 \times XH_2O$ or $Ba(NO_3)_2$ solution using incipient wetness technique. The mixture was dried at 80° C. in a vented oven. The dried catalyst was calcined in a muffle furnace at 300° C. for 4 h, ramp rate 1° C./min, in air.

The support, or the La/Ba impregnated support, was subsequently impregnated with Cu at ambient conditions, in a porcelain dish mixed in a lab-shaker with the appropriate concentration of $Cu(NO_3)_2 \times 2.5H_2O$ solution using incipient wetness technique. The mixture was dried at 80° C. in a vented oven. The dried catalyst was calcined in a muffle furnace at 300° C. for 4 h at a ramp rate of 1° C./min in air. The calcined Cu impregnated catalyst was sieved to 0.125-0.160 mm. The catalyst was reduced using 5% $H_2$ in $N_2$ at temperatures determined by differential scanning calorimetry (DSC) analysis (1-2 dwells at 180-330° C., dwell time=2 h, cooling to ambient temperature under $N_2$.)

Reactor Operation Procedure

Unless otherwise specified, the reactions described in the following examples were carried out in a stainless steel (SS316) continuous trickle bed reactor (ID=0.4 cm) using the following procedure:

The reactor was packed with approximately 1 mL of catalyst. If the catalyst was not pre-reduced the following procedure was used for in situ reduction: the reactor was heated at a rate of 1° C./min under forming gas (5% $H_2$ in $N_2$) to the desired reduction temperature (see examples), where it was held for the desired hold-up time, typically 2-3 hours. The pre-reduced or in-situ reduced catalyst was used for running multiple reactions under varying reaction conditions (temperature, pressure, feed concentrations). The reactor temperature was adjusted to the target first temperature and held overnight under forming gas and either water or aqueous substrate solution. Subsequently the first reaction condition started by changing the gas feed to 100% $H_2$ and the liquid feed to the desired aqueous substrate concentration. The liquid volumetric feed rate was adjusted to correspond to a target liquid hourly space velocity (LHSV), which was measured in units of mL liquid feed/mL catalyst/h. Unless otherwise specified, the ratio of the gas volumetric flowrate to the liquid volumetric flowrate as measured at ambient conditions (gas to oil ratio, GTO) was adjusted to a value of 4,000. Liquid effluent samples at each reaction condition were taken after continuous operation for a minimum of 24 hours. The liquid samples were analyzed by quantitative GC analysis.

Analytical Methods

Samples of reaction solutions were diluted with n-propanol, filtered through a standard 5 μm disposable filter, and analyzed by GC and GC/MS analysis using standard GC and GC/MS equipment: Agilent 5975C, HP5890, Stabilwax Column Restek Company Bellefonte, Pa. (30 m×0.25 mm, 0.5 micron film thickness). Chemical components of reaction product mixtures were identified by matching their retention times and mass spectra to those of authentic samples.

Example 1

In a stainless steel (SS316) pressure reactor 6 g of isosorbide was dissolved in 14 mL of water and combined with 1 g of catalyst ($CuO/ZnO/Al_2O_3$, Suedchemie Actisorb® 301). The reactor was connected to a high pressure gas manifold and the content was purged with nitrogen gas (1000 psi, 6.89 MPa) three times before hydrogen was added. About 600 psi (4.14 MPa) of hydrogen was added and the reactor was heated to 250° C. and final adjustments to the pressure were made by adding more hydrogen to reach the target pressure of 1000 psi (6.89 MPa). After 16 h, the reactor was allowed to cool to room temperature within 2 h and depressurized. The reaction product mixture was filtered through a standard 5 μm disposable filter and a sample was analyzed as described above. Results for the reactor effluent are given in Table 1.

TABLE 1

| Composition of Product Solution for Example 1 | | | | | | | |
|---|---|---|---|---|---|---|---|
| TDM (wt %) | 1,2CHD (wt %) | Linear $C_5/C_6$ diols (wt %) | THPM (wt %) | 1,2PDO (wt %) | Isosorbide (wt %) | Isosorbide Isomers (wt %) | Other alcohols and unknowns (wt %) |
| 26 | 2 | 3 | 2 | 7 | 43 | 8 | 8 |

Examples 2-8

About 0.75 mL of a 10 wt % aqueous solution of isosorbide was combined with the target amount of catalyst ($CuO/ZnO/Al_2O_3$, SuedChemie ActiSorb® 301) as indicated in Table 2 and placed in a glass vial equipped with a magnetic stir bar and having a perforated septum to limit vapor transfer rates. The vials were placed in a stainless steel (SS316) parallel pressure reactor (8 individual wells). The reactor was connected to a high pressure gas manifold and the content was purged with nitrogen gas (1000 psi, 6.89 MPa) three times before hydrogen was added. About 600 psi (4.14 MPa) of hydrogen was added and the reactor was heated to 250° C.; final adjustments to the pressure were made by adding more hydrogen to reach the target pressure of about 1000 psi (6.89 MPa).

After 4 h, the reactor was allowed to cool to room temperature within 2 h and depressurized. The reaction solution was diluted with n-propanol, filtered through a standard 5 μm disposable filter and a sample was taken, and analyzed as described above. Results for the reactor effluent are given in Table 2. In these Examples, 1,2PDO was not observed.

TABLE 2

Analysis of product solutions from Examples 2-8

Reactor Effluent Composition (wt %)

| Ex. | Catalyst Amount (mg) | TDM | 1,2CHD | Linear $C_5/C_6$ diols | THPM | Isosorbide | Isosorbide Isomers | Other alcohols and unknowns (wt %) |
|---|---|---|---|---|---|---|---|---|
| 2 | 10  | 3  | <1 | 3 | <1 | 82 | 2  | 8  |
| 3 | 20  | 7  | <1 | 2 | <1 | 78 | 3  | 8  |
| 4 | 40  | 16 | <1 | 4 | 1  | 49 | 7  | 22 |
| 5 | 80  | 20 | <1 | 4 | 1  | 43 | 14 | 16 |
| 6 | 120 | 25 | 2  | 5 | 1  | 32 | 19 | 15 |
| 7 | 160 | 27 | 2  | 3 | 1  | 24 | 27 | 16 |
| 8 | 200 | 32 | 2  | 8 | 2  | 7  | 12 | 32 |

Example 9

The reactor was charged with $CuO/ZnO/Al_2O_3$ (SuedChemie Actisorb®301) catalyst. The catalyst was reduced in situ at 250° C. for 3 h. A 2.5 wt % aqueous solution of isosorbide was used as the liquid feed. The liquid feed volumetric feed rate corresponded to a liquid hourly space velocity (LHSV) equal to 0.5 mL liquid feed/mL catalyst/h.

Product yields at different temperatures are given in Table 3 for 240° C.-280° C. under 100 bar $H_2$ pressure. The molar yields for tetrahydrofuran-2,5-dimethanol (TDM) ranged from 7% to 30%.

TABLE 3

Results for Example 9

| Temp. (° C.) | Product Molar Yields (mole %) | | | | Conv. (%) | Mole Balance (%) |
|---|---|---|---|---|---|---|
|  | TDM | THPM | 126HT | 1,6HD | | |
| 240 | 7.32  | 3.91  | 1.08 | 0.56 | 63.30 | 51.60 |
| 260 | 15.76 | 9.09  | 0.94 | 2.34 | 63.94 | 72.29 |
| 280 | 29.75 | 16.07 | 0.00 | 4.85 | 97.46 | 66.96 |

Example 10

The reactor was charged with $CuO/Cr_2O_3$ (SuedChemie T-4466) catalyst. A 2.5 wt % aqueous solution of isosorbide was used as the liquid feed. The catalyst was reduced in situ at 250° C. for 3 h. The liquid feed volumetric feed rate corresponded to a liquid hourly space velocity (LHSV) equal to 0.5 mL liquid feed/mL catalyst/h.

Product yields at different temperatures are given in Table 4 for 240° C.-280° C. under 100 bar $H_2$ pressure. The molar yields for TDM ranged from 8% to 14%.

TABLE 4

Results for Example 10

| Temp. (° C.) | Product Molar Yields (mole %) | | | | Conv. (%) | Mole Balance (%) |
|---|---|---|---|---|---|---|
|  | TDM | THPM | 126HT | 1,6HD | | |
| 240 | 8.13  | 4.15  | 1.41 | 0.64 | 72.61 | 43.89 |
| 260 | 22.73 | 10.26 | 0.55 | 3.11 | 82.62 | 62.31 |
| 280 | 13.98 | 14.55 | 0.00 | 6.28 | 98.24 | 52.46 |

Example 11

Hydrogenations of isosorbide were performed with commercial copper catalysts referred to as A-C, E, and G-O in the "Table of Commercially Available Materials Used and Their Sources" herein above. All catalysts were reduced in situ at 250° C. for 3 h.

A 2.5 wt % aqueous solution of isosorbide was used as the liquid feed for these runs. The liquid feed volumetric feed rate corresponded to a liquid hourly space velocity (LHSV) equal to 0.5 mL liquid feed/mL catalyst/h.

Product yields are given in Table 5 for 240° C.-280° C. under 100 bar $H_2$ pressure.

TABLE 5

Results for Example 11

| Catalyst | Temp. (° C.) | Product Molar Yields (mole %) | | | | Conv. (%) | Mole Balance (%) |
|---|---|---|---|---|---|---|---|
|  |  | TDM | THPM | 126HT | 1,6HD | | |
| A | 280 | 8.19  | 9.80  | 0.07 | 1.87 | 52.66 | 72.23 |
| B | 260 | 15.15 | 12.03 | 1.26 | 3.33 | 74.75 | 65.33 |
| C | 260 | 16.45 | 10.16 | 0.00 | 2.96 | 79.40 | 58.67 |
| E | 240 | 3.06  | 3.25  | 0.00 | 8.46 | 99.90 | 28.37 |
| G | 260 | 12.63 | 1.96  | 0.88 | 3.16 | 85.53 | 49.45 |
| H | 280 | 21.83 | 15.61 | 0.00 | 3.75 | 99.82 | 50.58 |
| I | 280 | 18.87 | 3.27  | 0.76 | 2.36 | 72.19 | 56.07 |
| J | 280 | 0.29  | 0.29  | 0.02 | 0.15 | N/A   | N/A   |
| K | 280 | 11.50 | 5.08  | 0.00 | 0.59 | 92.32 | 30.28 |
| L | 280 | 7.51  | 2.37  | 0.97 | 0.42 | 46.49 | 66.49 |
| M | 280 | 11.75 | 5.69  | 0.92 | 3.86 | 82.11 | 45.86 |
| N | 280 | 10.52 | 12.68 | 0.33 | 1.47 | 52.21 | 73.17 |
| O | 260 | 1.58  | 2.18  | 0.00 | 1.28 | 99.15 | 19.51 |

Example 12

Hydrogenations of isosorbide were performed with $CuO/SiO_2$ catalyst and the following mixtures of $CuO/SiO_2$ and heterogeneous acidic catalysts: $CuO/SiO_2$ (BASF Cu-0860), $CuO/SiO_2$ (BASF Cu-0860) intimately mixed with HY CBV780, $CuO/SiO_2$ (BASF Cu-0860) separately mixed with HY CBV780, $CuO/SiO_2$ (BASF Cu-0860) intimately mixed with $ZrO_2$, and $CuO/SiO_2$ (BASF Cu-0860) intimately mixed with $Nb_2O_5$. The mixed catalysts were prepared using the Catalyst Preparation Method I and Catalyst Preparation Method II. All catalysts were reduced in situ at 300° C. for 2 h.

A 2.5 wt % aqueous solution of isosorbide was used as the liquid feed for all the runs. The liquid feed volumetric feed rate corresponded to a liquid hourly space velocity (LHSV) equal to 0.5 mL liquid feed/mL catalyst/h. Product yields at different temperatures are given in Table 6 for 240° C.-280° C. under 100 bar $H_2$ pressure.

TABLE 6

Results for Example 12

| Catalyst | Temp. (° C.) | Product Molar Yields (mole %) | | | | Conv. (%) | Mole Balance (%) |
| --- | --- | --- | --- | --- | --- | --- | --- |
| | | TDM(*) | THPM | 126HT | 1,6HD | | |
| I | 240 | 0.75 | 0.00 | 0.13 | 0.00 | 20.60 | 80.30 |
| I | 260 | 3.85 | 0.00 | 0.17 | 0.00 | 52.00 | 52.00 |
| I | 280 | 46.98 | 1.81 | 0.00 | 0.74 | 91.20 | 59.90 |
| I, intimately mixed with P | 280 | 42.91 | 3.52 | 0.00 | 0.64 | 93.60 | 53.50 |
| I, separately mixed with P | 280 | 43.22 | 1.91 | 0.00 | 0.54 | 84.70 | 61.00 |
| I, intimately mixed with Q | 280 | 41.89 | 4.58 | 0.00 | 2.77 | 99.30 | 57.90 |
| I, intimately mixed with R | 280 | 46.36 | 3.47 | 0.00 | 1.34 | 97.60 | 53.50 |

(*)The reported TDM yields include yields to two isomers (cis- and trans-TDM).

Example 13

Reactor runs were performed with the following commercial copper catalysts mixed with heterogeneous acidic catalysts: CuO/ZnO (SuedChemie T-2130) intimately mixed with HY CBV780, CuO/ZnO (SuedChemie T-2130) intimately mixed with $ZrO_2WO_3$, CuO/NiO (Shepherd Chemical LB 3307) intimately mixed with $ZrO_2$, and $CuO/MnO_2$ (SuedChemie T-4489) intimately mixed with $ZrO_2WO_3$. The catalysts were prepared using the Catalyst Preparation Method II. All catalysts were reduced in situ at 300° C. for 2 h.

A 2.5 wt % aqueous solution of isosorbide was used as the liquid feed for all the runs. The liquid feed volumetric feed rate corresponded to a liquid hourly space velocity (LHSV) equal to 0.5 mL liquid feed/mL catalyst/h. Product yields are given in Table 7 for 240° C.-260° C. under 100 bar $H_2$ pressure.

TABLE 7

Results for Example 13

| Catalyst | Temp. (° C.) | Product Molar Yields (mole %) | | | | Conv. (%) | Mole Balance (%) |
| --- | --- | --- | --- | --- | --- | --- | --- |
| | | TDM(*) | THPM | 126HT | 1,6HD | | |
| G, intimately mixed with P | 260 | 11.90 | 0.00 | 0.00 | 0.30 | 84.00 | 32.10 |
| G intimately mixed with X | 260 | 44.37 | 5.79 | 0.00 | 3.22 | 97.80 | 55.60 |
| O, intimately mixed with Q | 260 | 10.84 | 3.62 | 0.00 | 0.59 | 99.60 | 15.50 |
| E, intimately mixed with X | 240 | 21.99 | 1.01 | 0.83 | 0.99 | 93.00 | 33.40 |

(*)The reported TDM yields include yields to two isomers (cis- and trans-TDM).

Example 14

The following supported copper catalysts were prepared using the Catalyst Preparation Method III: Sasol Alumina 3% La 7% Cu, Sasol Alumina 3% La 15% Cu, $ZrO_2$ 7% La 7% Cu, $ZrO_2$ 7% Ba 7% Cu, MEL Ce/$Zr_2O_3$ 3% Cu, MgO 3% Cu, HY CBV780 12% La 15% Cu, and HY CBV780 12% Ba 15%.

A 2.5 wt % aqueous solution of isosorbide was used as the liquid feed for all the runs. The liquid feed volumetric feed rate corresponded to a liquid hourly space velocity (LHSV) equal to 0.5 mL liquid feed/mL catalyst/h. Product yields are given in Table 8 for 240° C.-280° C. under 100 bar $H_2$ pressure.

TABLE 8

Results for Example 14

| Catalyst | Temp. (° C.) | Product Molar Yields (mole %) | | | | Conv. (%) | Mole Balance (%) |
|---|---|---|---|---|---|---|---|
| | | TDM(*) | THPM | 126HT | 1,6HD | | |
| S, with 7% Cu | 280 | 21.18 | 0.81 | 0.00 | 1.94 | 78.20 | 84.20 |
| S, with 15% Cu | 280 | 27.39 | 1.33 | 0.77 | 1.12 | 73.07 | 104.04 |
| Q, with 7% La & 7% Cu | 280 | 22.53 | 2.51 | 0.00 | 2.18 | 98.10 | 73.40 |
| Q, with 7% Ba & 7% Cu | 240 | 2.14 | 0.00 | 1.46 | 0.00 | 40.70 | 82.60 |
| U, with 3% Cu | 260 | 15.81 | 0.84 | 1.28 | 1.38 | 82.21 | 86.13 |
| V, with 3% Cu | 260 | 26.93 | 0.59 | 0.57 | 4.81 | 81.78 | 93.71 |
| P, with 12% La & 15% Cu | 260 | 7.66 | 0.00 | 0.00 | 0.00 | 11.91 | 98.73 |
| P, with 12% Ba & 15% Cu | 280 | 32.27 | 2.39 | 0.18 | 1.52 | 75.96 | 90.09 |

(*)The reported TDM yields include yields to two isomers (cis- and trans-TDM).

Example 15

Reactor runs were performed with the following commercial copper catalysts referred to as A-H and M-N in the "Table of Commercially Available Materials Used and Their Sources" herein above. All catalysts were reduced in situ at 250° C. for 3 h.

A 2.5 wt % aqueous TDM feed solution was used as the liquid feed for these runs. The liquid feed volumetric flowrate corresponded to a liquid hourly space velocity (LHSV) equal to 0.5 mL liquid feed/mL catalyst/h. Product yields for the various catalysts are given in Table 9 for 260° C.-280° C. under 100 bar $H_2$ pressure.

TABLE 9

Results for Example 15

| Catalyst | Temp. (° C.) | Product Molar Yields (mole %) | | | | | | | Conv. (%) | Mole Balance (%) |
|---|---|---|---|---|---|---|---|---|---|---|
| | | THPM | 126HT | 1,6HD | c12CHD | t12CHD | 1,5HD | 1,5PD | | |
| A | 280 | 28.39 | 0.85 | 10.89 | 0.83 | 1.12 | 4.64 | 2.46 | 12.85 | 137.05 |
| B | 280 | 8.83 | 0.55 | 11.93 | 3.25 | 4.86 | 1.99 | 1.46 | 53.82 | 79.23 |
| C | 280 | 10.27 | 0.50 | 10.09 | 2.33 | 3.76 | 1.67 | 1.30 | 40.99 | 89.66 |
| D | 280 | 12.75 | 0.25 | 17.42 | 4.86 | 6.94 | 3.02 | 1.61 | 60.66 | 87.26 |
| E | 260 | 16.97 | 0.23 | 11.10 | 1.73 | 4.22 | 0.22 | 1.83 | 99.29 | 37.88 |
| F | 280 | 9.81 | 0.42 | 8.17 | 1.86 | 2.75 | 1.51 | 1.25 | 34.87 | 91.69 |
| G | 280 | 3.52 | 0.41 | 14.50 | 6.85 | 15.68 | 5.37 | 4.20 | 63.58 | 87.49 |
| H | 280 | 15.03 | 0.48 | 7.16 | 1.47 | 2.05 | 1.20 | 1.11 | 27.07 | 102.05 |
| M | 280 | 7.86 | 0.42 | 11.50 | 7.76 | 15.92 | 1.85 | 3.97 | 78.44 | 74.44 |
| N | 280 | 4.93 | 0.62 | 3.44 | 0.59 | 1.15 | 0.37 | 0.74 | 10.29 | 101.93 |

Example 16

Reactor runs were performed with commercial copper catalysts mixed with heterogeneous acidic catalysts. The catalysts were prepared using the Catalyst Preparation Method II. All catalysts were reduced in situ at 300° C. for 2 h. A 2.5 wt % aqueous solution of TDM was used as the liquid feed for all the runs. The liquid feed volumetric feed rate corresponded to a liquid hourly space velocity (LHSV) equal to 0.5 mL liquid feed/mL catalyst/h. Product yields are given in Table 10 for 240° C.-280° C. under 100 bar $H_2$ pressure.

TABLE 10

Results for Example 16

| Catalyst | Temp. (° C.) | Product Molar Yields (mole %) | | | | | | | Conv. (%) | Mass Balance (%) |
|---|---|---|---|---|---|---|---|---|---|---|
| | | THPM | 126HT | 1,6HD | c12CHD | t12CHD | 1,5HD | 1,5PD | | |
| I, intimately mixed with X | 280 | 2.55 | 0.28 | 0.49 | 0.00 | 0.00 | 0.00 | 0.00 | 23.30 | 105.10 |

TABLE 10-continued

Results for Example 16

| Catalyst | Temp. (° C.) | Product Molar Yields (mole %) | | | | | | Conv. (%) | Mass Balance (%) |
|---|---|---|---|---|---|---|---|---|---|
| | | THPM | 126HT | 1,6HD | c12CHD | t12CHD | 1,5HD | 1,5PD | | |
| E, intimately mixed with X | 240 | 3.78 | 1.38 | 2.24 | 0.00 | 1.68 | 0.00 | 0.00 | 44.60 | 95.00 |
| E, intimately mixed with X | 260 | 22.85 | 0.00 | 12.88 | 2.82 | 5.32 | 1.39 | 0.00 | 83.60 | 75.00 |
| G, intimately mixed with P | 280 | 8.60 | 0.00 | 4.92 | 3.78 | 8.06 | 1.07 | 0.00 | 70.90 | 77.60 |
| G, intimately mixed with X | 240 | 1.73 | 0.32 | 0.63 | 0.00 | 0.00 | 0.00 | 0.00 | 8.50 | 108.60 |
| G, intimately mixed with X | 280 | 23.71 | 0.00 | 15.48 | 0.91 | 2.05 | 0.00 | 0.00 | 86.20 | 66.60 |

Example 17

The following supported copper catalysts were prepared using the Catalyst Preparation Method III: Sasol Alumina 10% La 3% Cu, Sasol Alumina 10% La 7% Cu, MEL Ce/ZrO$_2$ 7% Cu, MEL Ce/ZrO$_2$ 15% Cu, MgO 3% Cu, MgO 7% Cu, ZrO$_2$ 15% Cu 15% La, and HYCBV780 15% Cu 12% Ba.

Aqueous solutions (2.5 wt % or 10 wt %) of TDM were used as the liquid feed for all the runs. The liquid feed volumetric feed rate corresponded to a liquid hourly space velocity (LHSV) equal to 0.5 mL liquid feed/mL catalyst/h. Product yields are given in Table 11 for 260° C.-280° C. under 100 bar H$_2$ pressure.

TABLE 11

Results for Example 17

| Catalyst | Conc. wt % TDM | Temp. (° C.) | Product Molar Yields (mole %) | | | | | | | Conv. (%) | Mass Balance (%) |
|---|---|---|---|---|---|---|---|---|---|---|---|
| | | | THPM | 126HT | 1,6HD | c12CHD | t12CHD | 1,5HD | 1,5PD | | |
| T with 3% Cu | 2.5 | 280 | 3.17 | 0.08 | 3.19 | 2.23 | 3.58 | 0.00 | 1.42 | 27.46 | 121.22 |
| T with 7% Cu | 2.5 | 280 | 3.84 | 0.61 | 5.85 | 3.22 | 5.59 | 1.28 | 1.74 | 14.71 | 112.82 |
| U, with 7% Cu | 10 | 280 | 4.47 | 0.52 | 3.95 | 9.39 | 18.04 | 0.44 | 2.09 | 78.64 | 91.83 |
| U, with 15% Cu | 10 | 280 | 3.43 | 0.11 | 4.76 | 13.44 | 24.59 | 1.06 | 2.49 | 96.78 | 71.30 |
| V, with 3% Cu | 10 | 260 | 0.55 | 3.16 | 5.29 | 0.72 | 1.20 | 0.86 | 1.47 | 21.46 | 119.93 |
| V, with 7% Cu | 2.5 | 280 | 2.14 | 0.63 | 30.74 | 2.78 | 5.75 | 4.96 | 3.50 | 80.75 | 90.77 |
| Q, with 15% Cu & 15% La | 2.5 | 280 | 1.29 | 0.45 | 3.54 | 12.19 | 23.97 | 1.31 | 1.41 | 93.35 | 75.74 |
| P, with 15% Cu & 12% Ba | 2.5 | 280 | 24.20 | 0.54 | 10.49 | 0.00 | 0.00 | 0.00 | 0.00 | 44.76 | 111.65 |
| P, with 15% Cu & 12% Ba | 10 | 280 | 5.62 | 0.19 | 1.65 | 0.00 | 0.00 | 0.46 | 0.89 | 17.64 | 115.45 |

What is claimed is:

1. A process comprising:
    a) contacting isosorbide with hydrogen in the presence of a first hydrogenation catalyst at a first temperature between about 150° C. and about 400° C. and at a first pressure between about 500 psi to about 5000 psi to form a first product mixture comprising tetrahydrofuran-2,5-dimethanol.

2. The process of claim 1, wherein the first product mixture further comprises 1,6-hexanediol.

3. The process of claim 1, further comprising:
    b) heating the first product mixture in the presence of hydrogen and a second hydrogenation catalyst at a second temperature between about 120° C. and about 350° C. to form a second product mixture comprising 1,6-hexanediol.

4. The process of claim 3, wherein the first and second hydrogenation catalysts are the same.

5. The process of claim 1, wherein the catalyst comprises copper.

6. The process of claim 1, wherein the catalyst comprises CuO.

7. The process of claim 1, wherein the catalyst comprises from 2 weight percent to 98 weight percent CuO, and further comprises from 98 weight percent to 2 weight percent of at least one oxide selected from the group consisting of zinc oxide, magnesium oxide, barium oxide, chromium oxide, silica, alumina, zirconium dioxide, nickel oxide, manganese oxide, sodium oxide, potassium oxide, cerium oxide, lanthanum oxide, iron oxide, silver oxide, and cobalt oxide, based on the total weight of the catalyst.

8. The process of claim 7, wherein the catalyst further comprises magnesium oxide.

9. The process of claim 7, wherein the catalyst further comprises zinc oxide.

10. The process of claim 1, wherein the catalyst comprises $BaO/CuO/Cr_2O_3/SiO_2$, $BaO/CuO/Cr_2O_3$, $BaO/CuO/MnO_2/Cr_2O_3$, $CuO/SiO_2$, $CuO/Al_2O_3$, $CuO/NiO/Al_2O_3$, $CuO/Cr_2O_3/MnO_2$, $CuO/Cr_2O_3$, $CuO/MnO_2$, $CuO/Cr_2O_3$, $CuO/SiO_2/Cr_2O_3/MgO$, $CuO/NiO$, or $NiO/CuO/K_2O/Cr_2O_3/CaF_2$.

11. The process of claim 1, wherein the catalyst comprises $CuO/ZnO/Al_2O_3$.

12. The process of claim 1, wherein the first product mixture further comprises one or more of 1,2,6-hexanetriol and 2-hydroxymethyltetrahydropyran.

13. The process of claim 3, wherein the second product mixture further comprises one or more of 1,2,6-hexanetriol, 1,2-cyclohexanediol, 1,5-pentanediol, and 1,5-hexanediol.

14. The process of claim 7, wherein the first temperature is between about 200° C. and about 290° C. and the first pressure is between about 1000 psi and about 2000 psi.

15. The process of claim 3, wherein the second hydrogenation catalyst comprises from 2 weight percent to 98 weight percent CuO, and further comprises from 98 weight percent to 2 weight percent of at least one oxide selected from the group consisting of zinc oxide, magnesium oxide, barium oxide, chromium oxide, silica, alumina, zirconium dioxide, nickel oxide, manganese oxide, sodium oxide, potassium oxide, cerium oxide, lanthanum oxide, iron oxide, silver oxide, and cobalt oxide, based on the total weight of the catalyst.

* * * * *